United States Patent [19]
Lamar et al.

[11] Patent Number: 5,786,188
[45] Date of Patent: Jul. 28, 1998

[54] FUNGAL INOCULUM PREPARATION

[75] Inventors: Richard T. Lamar; Domen Lestan, both of Madison, Wis.; Christine E. Smith, Oxford, Pa.; Diane M. Dietrich, Madison, Wis.

[73] Assignee: The United States of America as represented by the Secretary of Agriculture, Washington, D.C.

[21] Appl. No.: 658,326

[22] Filed: Jun. 5, 1996

[51] Int. Cl.$^6$ .................. C12N 11/02; C12N 11/10; C12N 11/12; A01N 63/00

[52] U.S. Cl. .................. 435/177; 424/408; 424/484; 424/489; 424/490; 424/93.5; 435/174; 435/178; 435/179; 435/254.1; 435/911

[58] Field of Search .................. 424/408, 484, 424/489, 490, 93.5; 435/174, 254.1, 911, 177, 178, 179

[56] References Cited

U.S. PATENT DOCUMENTS

| | | | |
|---|---|---|---|
| 2,005,365 | 6/1935 | Di Giacinto | 47/1 |
| 2,761,246 | 9/1956 | Szuecs | 47/1.1 |
| 2,850,841 | 9/1958 | Szuecs | 47/1.1 |
| 4,083,144 | 4/1978 | Fuzisawa et al. | 47/1.1 |
| 4,420,319 | 12/1983 | Holtz et al. | 71/5 |
| 4,438,593 | 3/1984 | McNew et al. | 47/57.6 |
| 4,589,226 | 5/1986 | Stensaas | 47/58 |
| 4,668,512 | 5/1987 | Lewis et al. | 424/93 |
| 4,718,935 | 1/1988 | Walker et al. | 71/79 |
| 4,724,147 | 2/1988 | Marois et al. | 424/93 |
| 4,761,376 | 8/1988 | Kulpa et al. | 435/262 |
| 4,764,199 | 8/1988 | Pratt et al. | 71/5 |
| 4,767,441 | 8/1988 | Walker et al. | 71/79 |
| 4,776,872 | 10/1988 | Mulleavy et al. | 71/5 |
| 4,803,166 | 2/1989 | Kulpa et al. | 435/253.3 |
| 4,803,800 | 2/1989 | Romaine et al. | 47/1.1 |
| 4,818,530 | 4/1989 | Marois et al. | 424/93 |
| 4,891,320 | 1/1990 | Aust et al. | 435/262 |
| 4,922,650 | 5/1990 | Akao et al. | 47/1.1 |
| 5,053,332 | 10/1991 | Cook et al. | 435/178 |
| 5,068,105 | 11/1991 | Lewis et al. | 424/93 |
| 5,071,648 | 12/1991 | Rosenblatt | 424/78.06 |
| 5,100,800 | 3/1992 | Kulpa et al. | 435/264 |
| 5,360,607 | 11/1994 | Eyal et al. | 424/93.5 |
| 5,380,741 | 1/1995 | Hutt et al. | 514/383 |
| 5,476,788 | 12/1995 | Lamar et al. | 435/262.5 |
| 5,476,790 | 12/1995 | Blanchette et al. | 435/277 |
| 5,486,474 | 1/1996 | Bradley et al. | 435/262 |
| 5,518,921 | 5/1996 | Blanchette et al. | 435/277 |

OTHER PUBLICATIONS

P. Stamets, "Growing Gourmet and Medicinal Mushrooms," a companion guide to *The Mushroom Cultivator*, Ten Speed Press, pp. 151–152, Dec. 1993.

*Primary Examiner*—Michael G. Wityshyn
*Assistant Examiner*—Deborah Ware
*Attorney, Agent, or Firm*—Janet I. Stockhausen; M. Howard Silverstein; John D. Fado

[57] ABSTRACT

A fungal inoculum for bioaugmentation of soils contaminated with hazardous compounds or spawn for use in the edible mushroom industry is disclosed. A mechanically pelleted substrate that contains both structural and nutritive components forms the core of the fungal inoculum. The pelleted substrate core is coated with a hydrophilic material in which fungal propagules are dispersed. The biological potential of the fungal inocula can be enhanced by formulating the material composition of fungal inocula to meet the specific requirements of a particular fungus.

10 Claims, 6 Drawing Sheets

FUNGAL INOCULUM PREPARATION

FIELD OF THE INVENTION

The field of the present invention is fungal inoculum preparations. Specifically, the field of the present invention is inoculum pellets coated with a hydrophilic suspension containing fungal propagules.

BACKGROUND

Fungal Inocula

There is a great interest in different types of carriers of fungal inocula for uses such as biological control, fungal spawn, introduction of mycorrhizal fungi, and bioaugmentation. For example, carriers of fungal inocula for biological control include alginate hydrogel, with or without an additional nutrient source, (Walker, H. L. and W. J. Connick, *Weed Sci.* 31:333–338, 1983) and vermiculite (Walker, H. L., *Weed Sci.* 29:342–345, 1981). Examples of carriers for mycorrhizal fungal inocula include alginate hydrogel, with or without an additional nutrient source, (Mauperin, C. H., et al., *Can. J. Bot.* 65:2326–2329, 1987) and vermiculite and peat (Le Tacon, F., et al., *Can. J. Bot.* 63:1664–1668, 1985). Examples for carriers of fungal inocula for fungal spawn include grain, sawdust-grain mixtures, vermiculite saturated with nutrient broth (Stamets, P., *Growing Gourmet and Medical Mushrooms*, Ten Speed Press, Berkeley, 1993) and alginate hydrogel (Romaine, C. P. and B. Schlagnhaufer, *Appl. Environ. Microbiol.* 58:3060–3066, 1992). Examples of carriers of fungal inocula for bioaugmentation of contaminated soil are described below.

Bioremediation

The use of lignin-degrading basidiomycetes for remediation of soils contaminated with hazardous organic compounds has been studied extensively (Davis, M. W., et al., *Environ. Sci. Technol.* 27:2572–2576, 1993; Lamar, R. T., et al., *Soil Biol. Biochem.* 26:1603–1611, 1994; Lamar, R. T., et al., *Appl. Environ. Microbiol.* 56:3039–3100, 1990; Lamar, R. T., et al., *J. Indust. Microbiol.* 9:181–191, 1992; Lamar R. T., et al., *Environ. Sci. and Technol.* 27:2566–2571, 1993; Lamar, R. T., et al., *Soil Biol. Biochem.* 22:433–440, 1990; Lamar, R. T., et al., In G. F. Leatham (ed.) *Frontiers in Industrial Mycology.* Chapman & Hall, New York, p. 127–143, 1992; Lamar, R. T., et al., *Appl. Environ. Microbiol.* 56:3519–3526, 1990; Loske, D., et al., In M. P. Coughlan and M. T. A. Collaco (ed.), *Advances in Biological Treatment of Lignocellulosic Materials.* Elsevier, London and New York, p. 311–322, 1990; Morgan, P., et al., *Soil Biol. Biochem.* 25:279–287, 1993).

The salient feature that makes these organisms attractive as microbial agents in bioremediation is their ability to degrade a wide variety of hazardous compounds (Lamar, R. T., et al., supra, 1992). Despite this recognized potential, development of fungal bioaugmentation for use on an industrial scale has been hampered by inconsistent treatment results in the field. One of the primary factors leading to variable treatment effectiveness is the approach to inoculum formulation, production, delivery, and application to soil.

Currently, lignin-degrading fungi are delivered to soil via various organic substrates such as wood chips, wheat straw, corn cobs, commercial mushroom spawn and other agricultural products that are thoroughly grown through with selected fungi (Fernando, T., et al., *Appl. Environ. Microbiol.* 56:1666–1671, 1990; Loske, D., et al., supra, 1990; Okeke, B.C., et al., *Biotechnol. Lett.* 15:1077–1080, 1993; Šašek, V., et al., *Biotechnol. Lett.* 15:521–526, 1993). Inocula produced using these materials as solid substrate supports have low inoculum potential (fungal biomass produced per weight or volume of inoculum), are of inconsistent quality, relatively expensive to produce (e.g. $2.5 Kg$^{-1}$ for commercial mushroom spawn), and are mostly water by weight (e.g. 60% moisture content).

Low inoculum potential necessitates the production and application of vast quantities of inoculum. Application rates have commonly ranged from 10% to 40% dry weight of inoculum per dry weight of soil. Also, maintenance of inoculum potential of these inocula during transportation and application has been difficult. Despite the use of refrigeration, "flashing" or the production of excessive amounts of metabolic heat has occurred during the transportation of large quantities of fungal inoculum (Lamar, R. T., et al., supra, 1994). This process reduces the inoculum potential through the consumption of nutrients that would normally be used to support fungal growth subsequent to soil application and by the destruction of fungal biomass as a result of elevated temperatures. Deterioration of inoculum potential during the application process as a result of the destruction of fungal biomass, has also been reported (Lamar, R. T., et al., supra, 1994).

The development of effective, low-cost fungal inocula that are engineered to maintain inoculum potential during transport and application is one of the keys to commercialization of fungal soil remediation. The art of fungal inoculation needs fungal inocula that use inexpensive substrates and uncomplicated procedures and equipment, that possess high inoculum potentials and that are physically and biologically robust enough to retain inoculum potential during transportation and application.

SUMMARY OF THE INVENTION

The construction of fungal inocula of the present invention begins with pelleting the proper formulation of materials, preferably agricultural and wood industry by-products. The effectiveness of fungal inocula in a bioaugmentation application to remove pentachlorophenol (PCP) in artificially contaminated soil was confirmed and is described below in the Examples.

In one embodiment the present invention is a fungal inoculum comprising a pelleted substrate coated with fungal propagules suspended in a hydrophilic material. Preferably, this hydrophilic material is a hydrogel, such as an alginate or alginic acid. Preferably, the fungal propagules have been allowed to form a mycelial mat over the surface of the pellet.

A preferable pelleted substrate comprises one or more structural components such as sawdust or rice hulls mixed with one or more nutrient sources such as starch, corn meal, or corn steep liquor. Structural components, such as sawdust, also provide nutrients. Preferably, lignosulfonate is added as a lubricant for pelleting. The composition of the components can be tailored to enhance the growth and/or the pollutant-degrading ability of the fungus.

In another embodiment, the present invention is a method of propagating a fungus comprising placing the fungal inoculum described above in a growth medium and allowing the fungus to propogate. In a particularly advantageous embodiment of the present invention, the growth medium is PCP-contaminated soil.

It is a feature of the present invention that a fungal inoculum with high mechanical strength is provided.

It is another feature of the present invention that a production of fungal inoculum with a high inoculum potential is provided.

It is another feature of the present invention that a fungal inoculum with a consistently high inoculum potential is provided.

It is another feature of the present invention that a fungal inoculum created from inexpensive substrates such as agricultural and wood industry by-products is provided.

It is another feature of the present invention that a fungal inoculum with good shipping and storage characteristics is provided.

Other features, advantages and characteristics of the present invention will become apparent after observation of the specification, claims and figures.

DESCRIPTION OF THE DRAWINGS

FIG. 1A pellets have not been inoculated.

FIG. 5A illustrates Marshan soil supplemented with sterile pellets. FIG. 5B illustrates Batavia soil inoculated with *P. chrysosporium*. FIG. 5C illustrates Marshan soil inoculated with *P. chrysosporium*. FIG. 5D illustrates Marshan soil inoculated with *P. sordida*. FIG. 5E illustrates Marshan soil inoculated with *I. lacteus*. FIG. 5F illustrates Marshan soil inoculated with *B. adusta*. FIG. 5G illustrates Marshan soil inoculated with *T. versicolor*.

DESCRIPTION OF THE INVENTION

1. In General

Figure 1A:
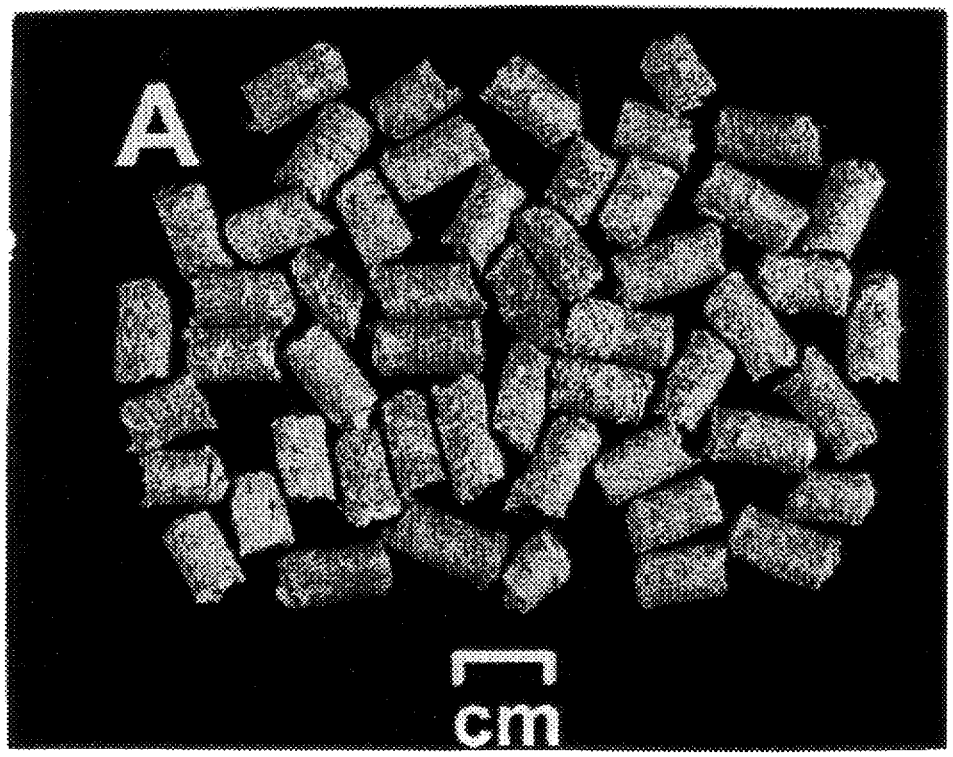
FIG. 1A and B is a photograph of pellets of the present invention. The FIG. 1A and B pellets are composed of 75% aspen sawdust, 15% potato starch, 8% corn meal and 2% Ca-lignosulfonate.
Figure 1B:
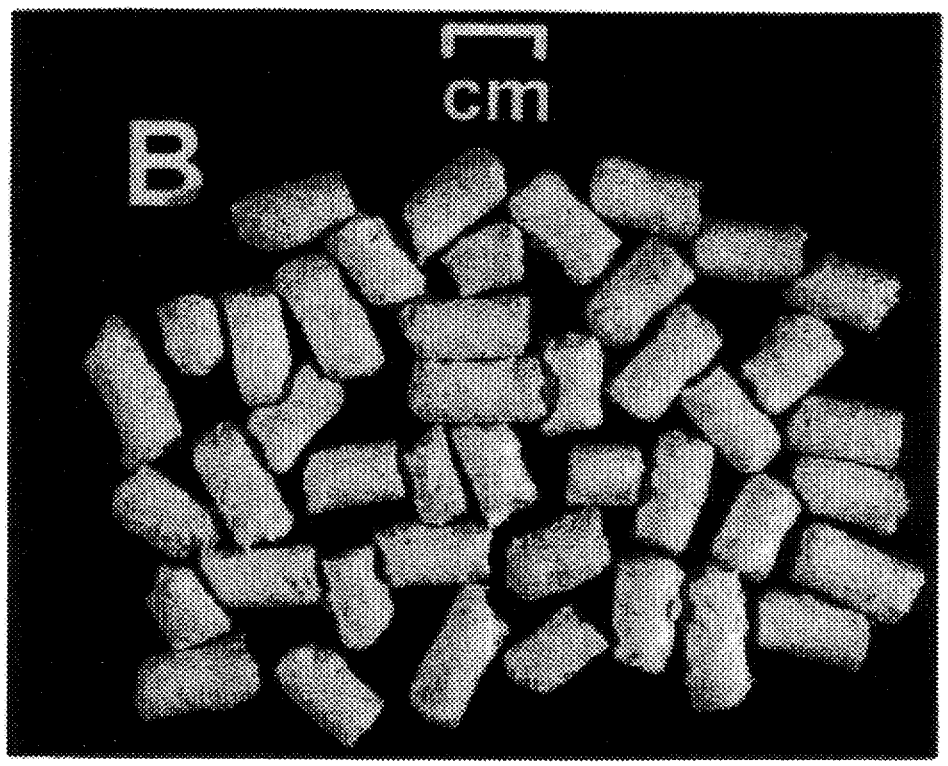
FIG. 1B pellets have been coated with a Na/alginate-mycelial fragment suspension and overgrown with 7-days-old *Irpex lacteus*.
Figure 2:
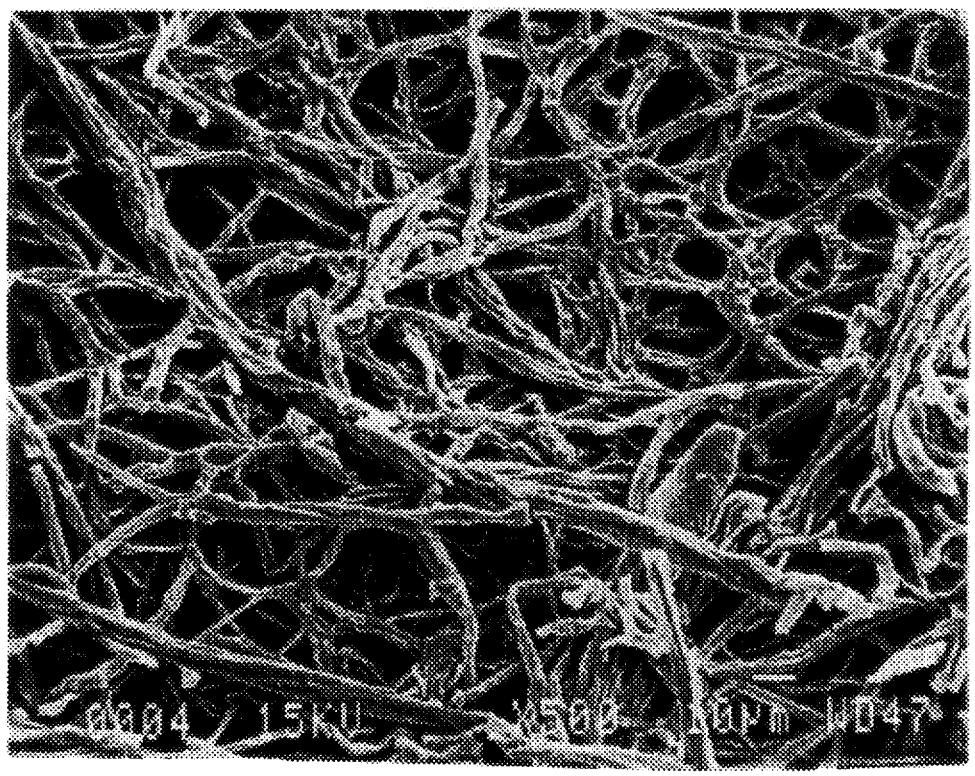
FIG. 2 is a photomicrograph (at 530 X) of the mycelium mat covering the pellets depicted in FIG. 1B.

Development and characterization of a novel fungal inoculum, preferably for bioaugmentation of soils contaminated with hazardous organic compounds or spawn for use in the edible mushroom industry, is presented. The inocula are in the form of pelleted solid substrates coated with a hydrophilic material, such as a hydrogel, containing a suspension of fungal propagules such as spores or mycelial fragments (see FIGS. 1A and 1B). These pellets are typically incubated until over-grown with fungal mycelia that are generated from propagules of the selected fungi (FIG. 2).

The pelleted fungal inocula meet criteria for successful commercial production and application to the soil: (i) the inocula are predominately made from inexpensive agricultural and wood industry by-products; (ii) the material composition of the inocula can be adjusted to meet the nutrient requirements of particular fungi; (iii) there is consistency in quality and fungal physiological state during inoculum production, storage, and transportation can be controlled; (iv) the fungal inocula resist competition and proliferation from indigenous soil microbes; (v) the inocula are lower in moisture content than current fungal inocula, thus decreasing the cost of transportation; (vi) the inocula have sufficient mechanical strength to allow handling, transportation, and introduction into the soil without change in mechanical consistency of the pellets; and (vii) the inocula can be produced with conventional procedures and machinery.

The present invention is suitable for the creation of an inoculum using a great many fungal structures. We refer to these fungal structures as fungal "propagules." A fungal propagule is defined herein as any vegetative or asexual or sexual structure of a fungus that is capable of growing into a new fungal colony, including but not limited to conidia, spores, chlamydospores, thallospores, basidiospores, ascospores, any other asexual or sexual spores, thalli, hyphae, rhizomorphs, homogenized and unhomogenized mycelium.

2. Pellets

Pellets suitable for the present invention are preferably comprised of four components. The first component is a structural matrix that imparts strength and durability and some nutritive value to the pellet. The second component is primarily a nutritive component that should allow the fungal propagules to grow and is composed of one or more substrates. The first and second component may be one single material, such as sawdust, which can act as both a structural matrix and a nutritive component.

The third component is a lubricant such as lignosulfonate, which acts as a lubricant in the pelleting process. The fourth component is a hydrophilic coating in which the fungal propagules are initially suspended.

As the Examples below indicate, the structural component of the pelleted present invention may be many different agricultural and wood industry by-products. As many different materials will work, it is most commercially attractive to select the least expensive material. Specifically, the Examples below demonstrate the suitability of both rice hulls and sawdust as suitable pellet making materials (see Table 1). Other suitable materials would be ground corn cobs, corn fiber, nut hulls, and soybean hulls.

It is important that the strength of the pellet after drying be at least 2 N or 0.04 J for successful mixing with soil. Greater strengths are especially preferred. Example 2 demonstrates a preferred method for measuring the mechanical strength of pelleted fungal inocula. In general, this mechanical strength was assessed by two independent methods. The first method measured the force needed to rupture the pellets by force gauges (spring scales) of various scales. The Example describes a preferred method of making this measurement. The second method which involves the impact energy that the structure of the pellet substrate could absorb before breaking down, was also determined with a specially designed instrument. The impact energy (W) was calculated after measuring the distance between a free falling block of steel of known mass and a fixed pellet and expressed in J (Joules).

Figure 3:
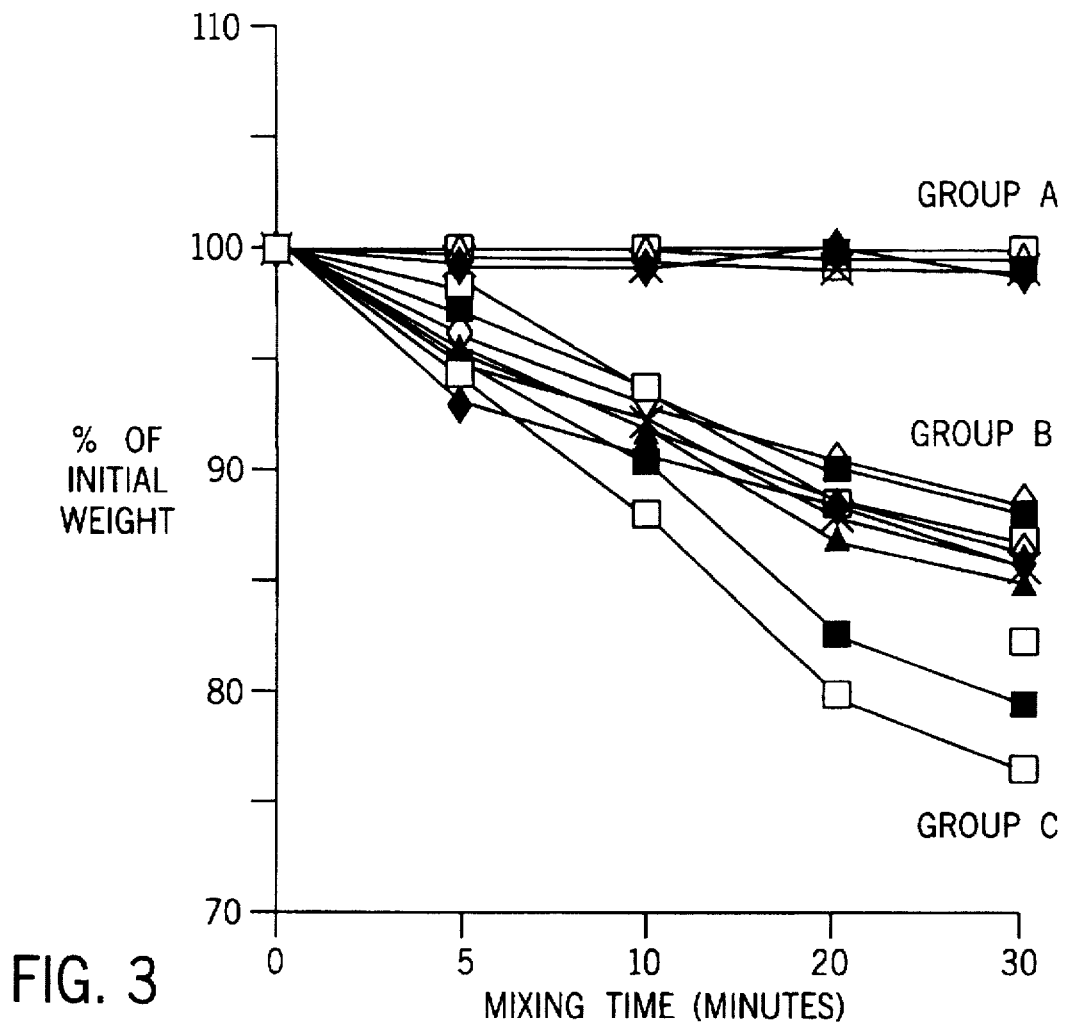
FIG. 3 is a graph showing the decrease of initial dry weight of pellets with different mechanical strengths after mixing 3% of pellets with 1 Kg of sand or soil during a 30 minute period.
Figure 4A:
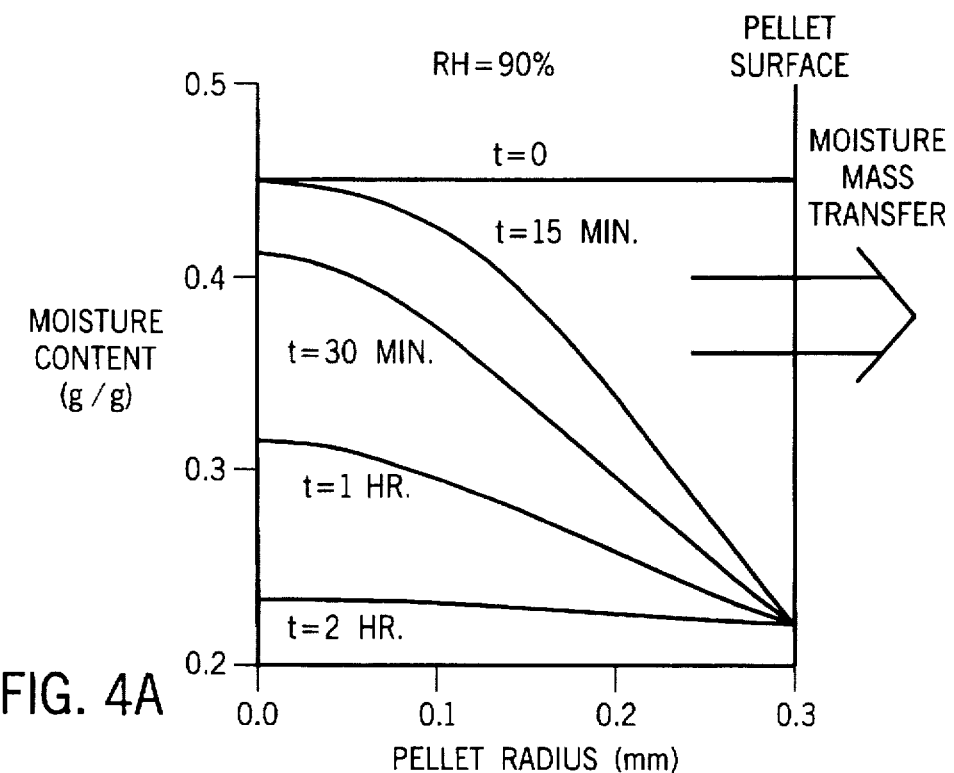
FIG. 4A–B is a diagram of a proposed simplified model for moisture distribution in a non-coated pellet (FIG. 4A) and pellet coated with alginate hydrogel (FIG. 4B).
Figure 4B:
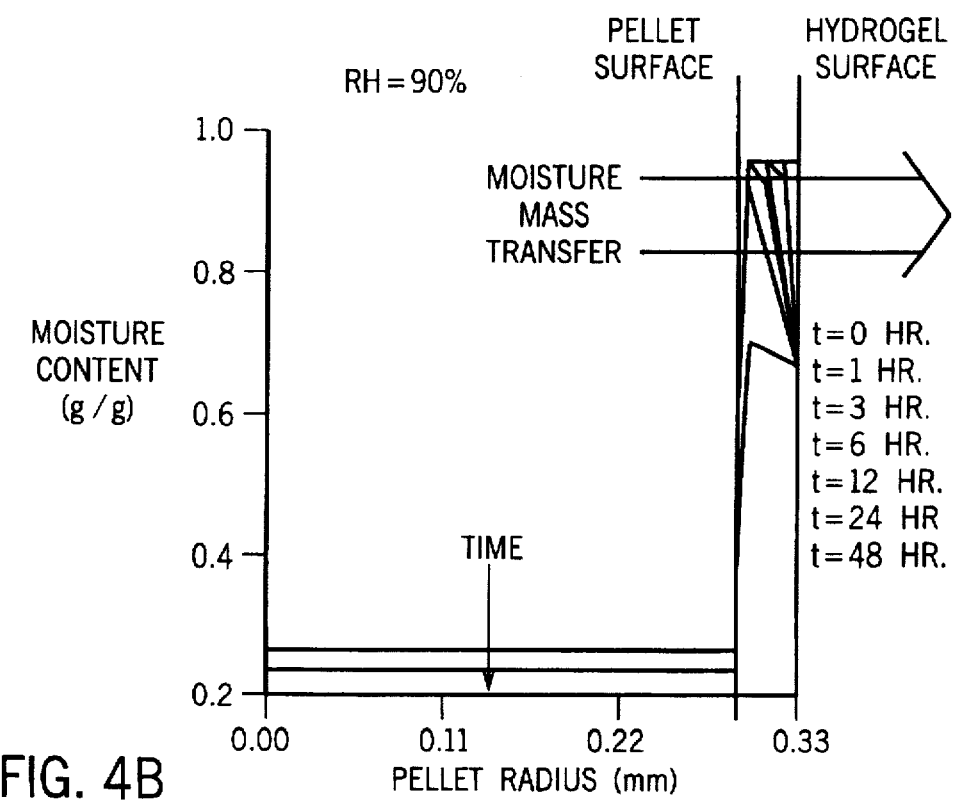

Table 1 lists a representative range of strength of pellets both before and after drying. FIG. 3 presents data obtained from experiments that simulated inoculation of soil with fungal inoculum by mixing the pellets with soil and sand in a laboratory mixer. FIG. 3 shows the decrease and initial dry weight.

The nutritive content of the pellet is important in allowing the fungus to grow. The Examples below demonstrate the usefulness of starch, corn meal, and corn steep liquor as nutritive substances.

As the Examples below indicate, between 8% and 83% of the initial pellet is preferably nutritive material. The nutritive component of the pellet is important for enhancing fungal growth beyond what would be obtained from the carrier component. It can be composed of one or more materials.

The Examples below demonstrate the usefulness of starch, corn meal, and corn steep liquor as nutritive substances. For a dry non-coated pellet, percentage ranges for the carrier (e.g. sawdust), nutritive (e.g. corn meal and starch), and lubricant components (e.g. lignosulfonate) are respectively, 15% to 90%, 8% to 83%, and 1% to 3%. An example formulation is as follows: 55% sawdust, 28% corn meal, 15% starch and 2% lignosulfonate. However, formulations will be varied in response to the fungal species and the conditions under which the inoculum will be used.

The nutritive and structural components of the pellets are mixed and then preferably sterilized, typically by autoclaving for 20 minutes at 120° C. The sterile substrates are preferably moistened to 20–30% and then pelleted (typically in a 500 g batch) using a laboratory scale pellet press. It is thus desirable to prevent contamination of the pelleted substrates. Therefore, the pellet press is preferably stationed in a positive pressure room with constant circulation of air through HEPA filters. Prior to use, the pellet press may also be decontaminated with ethanol and the room sterilized by exposure to UV lights.

The Examples below demonstrate that sterile substrates were effectively fed into the pellet press at a rate of approximately 500 g/min. using a dry material feeder. FIG. 1A is a photograph of exemplary pellets of the present invention. The pellet press is typically operated at a grinder roller speed of 120 rpm. The model pelleted substrate produced was 5 mm in diameter and averaged 8 mm in length. At this point, the pellets have a moisture content preferably between 20 and 35%. Most preferably, the pellets are between 27 and 30%.

Typically, batches of pelleted substrates are dried to a moisture content of below 20% in a sterile environment in a stream of hot air (approximately 80° C.) with a commercial variable temperature heat gun for 1 hour and then placed in sterile polyethylene bags and stored at –6° C. until further use. A preferable moisture content is between 3–10%.

The hydrophilic layer of the pellets initially contains suspended fungal propagules. Preferably, this coating comprises an alginate hydrogel with or without an additional nutrient source. Other suitable materials include any hydrogel such as agarose, chitosan, carrageenan, and gelatin or their derivates.

3. Infestation of the Pellets

The present invention requires that the pelleted substrate be infested with the fungus. One suitable method comprises growing the fungus of interest on an appropriate growth medium and then separating and preparing fungal propagules from that medium. One of skill in the art will recognize that there are many suitable methods for growing and preparing particular fungi. Example 2B describes medium and culture conditions for specific fungal strains used as examples. Example 2C describes fragmentation of fungal mycelia before suspension in sodium alginate.

The propagules are then mixed with a hydrogel, preferably an alginate or alginic acid. Example 2 below describes a typical method of suspending fungal propagules in sodium alginate. Preferably, a 2% deionized water solution of medium viscosity alginate (preferably sterilized by autoclaving for 10 minutes at 120° C.) is mixed with the fungal propagules. Preferably, known amounts of fungal biological material are added to the cooled alginate to form an alginate hydrogel suspension. (See Table 3, disclosing 3200 conidia/mL of hydrogel solution or 0.03 g–0.17 g homogenized mycelia/mL of hydrogel).

The propagule/hydrogel suspension is coated under sterile conditions onto the sterile pelletized substrate and subsequently polymerized with a 5% calcium chloride solution, forming a hydrogel coating on the pellet surface. This coating is preferably applied by spraying or dipping the pellets. These coated pellets are then incubated until the fungus thoroughly colonizes the surface of the pellets.

At this point, the moisture content of the pellets is preferably between 25–40%.

The Examples below describe a preferable method of incubating the pellets: the coated pellets are transferred to sterile polyethylene bags and incubated at suitable temperatures for growth of the particular fungal species until pellets were thoroughly overgrown with mycelium. FIG. 1B is a photograph of overgrown pellets of the present invention. FIG. 2 is a photomicrograph at 530 X of the mycelium mat coating the pellets in FIG. 1B.

4. Suitable Fungal Strains

The present invention is suitable for any fungal strain. The Examples below demonstrate the propagation of specific fungi, but the success of these exemplary fungi in the method demonstrates that any other fungus could substitute.

5. Propagation of Fungi Using the Inoculum

After preparing the fungal inoculum of the present invention, one will wish to use these inocula to propagate the fungus.

The Examples below describe the inoculation of soil culture preparations with the inoculum. These are, of course, exemplary preparations designed to show the efficacy of the present invention. To inoculate a growth medium, such as a contaminated soil, with pellets of the present invention one would simply mix the medium with the pellets. Alternatively, one could drop the pellets into the growth medium. One skilled in the art would know how to determine the inoculum application rate that would provide acceptable fungal growth in a growth medium.

The present invention is suitable for use as spawn for use in the edible mushroom industry. Currently, mushroom spawn is predominantly a grain or sawdust composition. One would use the present invention to create spawn for a commercial mushroom preparation, such as for the common button mushroom *Agaricus bisporous*. Pellets could be used to inoculate beds, trays, bags or blocks of compost substrate from which the mushrooms are currently propagated. Additionally, the present invention might be used to inoculate casing material (usually peat-based) which is applied to the compost during its cultivation cycle.

Spawn could be made in a similar way for other mushroom species including *Lentinus edodes*, Pleurotus spp., *Grifola frondosa*, *Flamulina velutipes* and *Pholiota nameko*. Typically, pellets containing these fungi would be inoculated into bags or bottles of a variety of substrates from which the mushrooms are currently propagated.

The present invention may also be used as inocula in the biopulping industry. Species used could include *Ceriporiopsis subvermispora* and *Phanaerochaete chrysosporium*.

EXAMPLES

1. In General

For bioaugmentation of soils contaminated with hazardous chemicals, *Phanerochaete chrysosporium* (BKM F-1767, ATCC 42725), *Phanerochaete sordida* (HHB-8922-Sp), *Irpex lacteus* (Mad-517, ATCC 11245), *Bjerkandera adusta* (FP-135160-Sp, ATCC 62023), and *Trametes versicolor* (MD-277) were evaluated.

Fungal inocula made with *Phanerochaete chrysosporium*, *Irpex lacteus*, *Bjerkandera adusta*, *Phanerochaete sordida* and *Trametes versicolor* inoculated at a rate of 3% in non-sterile soil, artificially contaminated with 100 mg/kg PCP, removed 85%, 86%, 82%, 90% and 92% of PCP in four weeks, respectively.

2. Materials and Methods

A. Organisms. *Phanerochaete chrysosporium* (BKM F-1767, ATCC 42725), *Phanerochaete sordida* (HHB-8922-Sp), *Irpex lacteus* (Mad-517, ATCC 11245), *Bjerkandera adusta* (FP-135160-Sp, ATCC 62023), and *Trametes versi-* color (MD-277) were obtained from the Center for Forest Mycology Research, Forest Product Laboratory, Madison, Wis. The fungi were grown and maintained on 2% potato-dextrose agar (PDA) (Sigma, St. Louis, Mo.).

B. Medium and culture conditions. *Phanerochaete chrysosporium* was cultured on 2% PDA at 30° C. for 7–10 days to produce conidia. The conidia were collected from agar plates with deionized, sterile water and the spore suspension was filtered through glass wool. Spore concentration was determined by measuring optical density of the spore suspension at 650 nm ($2.5 \times 10^6$ spores $mL^{-1}$ corresponds to $E_{650}$=0.5, (Kirk, T. K., et al., *Arch. Microbiol.* 117:277-285, 1978)). The spore suspension was then suspended in Na-alginate for coating of the pelleted substrate.

*Phanerochaete sordida*, *Irpex lacteus*, and *Bjerkandera adusta* were grown in 300-mL Erlenmeyer flasks containing 40 mL of growth medium with 2% glucose (Mallinckrodt, Paris, KT) and 2% malt-extract (Difco Laboratories, Detroit, Mich.) in stationary culture mode at 30° C. for 7–14 days to form a mycelial mat. The growth medium was inoculated with agar plugs taken from PDA plates.

*Trametes versicolor* was grown in 300-mL Erlenmeyer flasks containing 60 mL of growth medium with 2% glucose, 2% malt extract, and 0.1% Tween 80 in a rotary shaker at 250 rpm and 30° C. for 7–10 days to form mycelial pellets. The growth medium was inoculated with fungal fragments obtained from fragmentation of mycelial pellets or surface mat mycelia from stationary culture, obtained as described below.

C. Fragmentation of fungal mycelia. Surface mat mycelia from stationary-grown cultures or mycelial pellets from shake cultures of *T. versicolor* were filtered from the growth medium, washed with, and than resuspended in sterile, deionized water of equal volume to the original growth medium. The resulting mycelial suspensions were fragmented four times for 5 seconds at 22000 rpm in a laboratory blender. The dry weight of mycelial fragments in suspension was determined by collection of mycelial fragments on preweighed Whatman No. 1 filter, and weighing after drying at 60° C. for 24 hours. Mycelial fragments were then suspended in Na-alginate for coating of the pelleted substrates.

D. Conditioning of mycelial fragments. Sixty mL of *T. versicolor* mycelial fragment homogenate were added to an equal volume of growth medium containing 2% malt-extract and 2% glucose. The enriched suspension was then transferred to a sterile 300-mL Erlenmeyer flask and conditioned by incubation on rotary shaker, operated at 250 rpm and at 30° C., for 6–12 hours.

E. Sterilization and pelleting of substrate. Substrates for producing pellets were aspen sawdust, 25% moisture content (Walter Brothers, Holkum, Wis.), rice hulls, (Riceland, Stutgart, Ark.), and nutrient-fortified grain-sawdust mixture, (L. F. Lambert Spawn Co., Inc., Coatesville, Pa.). Substrate moisture contents were adjusted by adding the appropriate amount of deionized water. These carrier substrates were supplemented with starch (Staley, Decatur, Ill.), corn meal (CPC, Summit-Argo, Ill.), corn steep liquor (CPC, Summit-Argo, Ill.), and Calignosulphonate (Lignotech, Greenwich, Conn.).

Mixtures of these materials (see Table 1, below) were sterilized in 2800-mL Erlenmeyer flasks (250 g per flask) by autoclaving for 20 minutes at 120° C. Sterile substrates were moistened to 27–30%, and then pelleted, 500 g per batch, using a laboratory scale pellet press (Amandus Kahl Nachf., Hamburg). To prevent contamination of pelleted substrates the pellet press was stationed in a positive pressure room, with constant circulation of air through HEPA filters. Prior to use, the pellet press was decontaminated with 75% ethanol and the room was sterilized by exposure to UV light.

Sterile substrates were fed into the pellet press at a rate of approximately 500 g min.$^{-1}$ using a dry material feeder (Accu-Rate Inc., Whitewater, Wis.). The pellet press was operated at a grinder rollers speed 120 rpm. The model pelleted substrate produced was 5 mm in diameter and averaged 8 mm in length.

F. Drying and coating the pelleted substrate. Batches of pelleted substrate were dried to 3–10% moisture content in a sterile environment in a stream of hot air (approximately 80° C.) with a commercial variable temperature heat gun (Master Appliance, Racine, Ill.) for 1 hour, placed in sterile 60-mL polyethylene bags (Cole-Parmer, Niles, Ill.), and stored at −6° C. until further use.

Pellets from one polyethylene bag, 35–40 g of dried pellets, were coated with Na-alginate hydrogel containing fungal biomass under sterile conditions with a commercial spray gun (Wagner, Minneapolis, Minn.).

A deionized water solution of medium viscosity Na-alginate (Sigma, St. Louis, Mo.) was sterilized by autoclaving for 10 minutes at 120° C. (Šašek, V., et al., supra, 1993). Known amounts of fungal biological material which consisted either of conidia, chlamydospores and mycelial fragments, or only mycelial fragments of tested fungi were added to the cooled Na-alginate to form a 2% Na-alginate hydrogel solution. Different concentrations of fungal biological material in Na-alginate hydrogel including 0, 10-fold, 100-fold, 1000-fold, and 10,000-fold dilutions of the original conidia suspensions or mycelial fragment homogenates were tested for coating (Table 3, below).

Pellets were coated by consecutive spraying with alginate hydrogel-biological material suspension and small amounts of a 5% solution of sterile, analytical grade $CaCl_2$. Alginate hydrogel film was formed immediately on the pellets' surface when calcium ions cross-linked the alginate by electrostatic interactions with carboxylate groups of neighboring macromolecules (Abletshuauser, C. B., et al., *Journal of Controlled Release* 27:149–156, 1993). The amount of applied hydrogel was determined by weighing the pelleted substrate before and after spraying.

G. Viability of fungal spores and mycelial fragments propagules. Serial dilutions of 2% Na-alginate spore suspension or 2% Na-alginate mycelial fragments suspension in sterile deionized water were prepared. Aliquots of 0.2-mL were spread on Petri dishes with PDA (three plates per replicate per dilution). Germinating spores or fungal colonies from mycelial fragments were counted on the agar plates after 18 hours or 3 days of incubation at 30° C., respectively, and populations were reported as colony-forming units (CFU). A 1000-fold dilution of original Na-alginate spore and Na-alginate mycelial fragments suspension was found the most useful for colony counting.

H. Over-growing the pellets with fungal mycelium. Coated pellets were transferred to sterile 60-mL polyethylene bags, and incubated at 24° C. or 30° C. until pellets were determined to be thoroughly over-grown with mycelium by visual inspection.

I. Contamination of fungal inocula. The attack and proliferation of indigenous soil bacteria and fungi on fungal inocula introduced into the soil was studied with artificially PCP-contaminated soils, and with soils collected from actual contaminated sites (see Table 5, below). Coated pellets were inserted into the soil to approximately ¾ of their length and monitored for proliferation of inoculated fungi to the soil and for possible soilborne microbial contamination. The inoculated soils were incubated in jam jars (30 g of soil, 3 pellets per jar) with modified covers as described below, at 24° C. The microbial contaminants on pellets were identified by transferring pieces of contaminated pellets to PDA and malt-extract agar composed of 2% malt-extract and 1.5% Bacto Agar (Difco). The indigenous soil fungi were also identified on PDA and MEA plates, after inoculation of agar plates with soil pieces and with deionized sterile water soil extracts.

J. Mechanical strength of the pelleted fungal inoculum. Mechanical strength of the pellets, pellets coated with hydrogel, and pellets over-grown with fungal mycelium was assessed by two independent methods: (i) The force (F) needed to rupture the pellets was measured with force gauges (spring scales) of various scales: 10–250 N, 0–2000 N, and 0–15000 N (Osborn Inc., New York, N.Y.) and expressed in N (Newtons). One-half of the pellet was fixed in a clamp in the test stand equipped with a force gauge. The free half of the pellet was hooked to the force gauge. Force was imposed on the pellet by manually pulling the force gauge from the fixed pellet. The peak force at the moment of pellet rupture was measured; (ii) The impact energy which the structure of the pelleted substrate could absorb before breaking was also determined with a specially designed instrument. The impact energy (W) was calculated after measuring the distance between a free falling block of steel of known mass and a fixed pellet and expressed in J (Joules).

The adequate range of mechanical strength of pellets for successful inoculation into the soil was determined by simulating mixing of the inoculum with soil in a laboratory V-shaped mixer of 5 L capacity. Pellets of different mechanical strengths (1.94'±0.78 N and 0.02±0.01 J; 1.25±0.52N and 0.04±0.00 J; 17.51±4.94 N and 0.11±0.02 J) were mixed with sands of different particle size (fine, particles >2 mm, and coarse) and with Marshan soil of different moisture contents (3.5% and 40%), for different times. Fracture and abrasion of pellets was determined by measuring the decrease of initial dry weight of pellets after separation of pellets from soil by screening through 3 mm sieve.

K. Soil cultures preparation. A Marshan sandy loam and Batavia silty clay loam were collected from A and Bt2 horizons, respectively, air dried, crushed, mixed thoroughly, sifted through a 2.5 mm sieve, and stored in plastic bags at 4° C. The chemical characteristics and trace constituents of the soils are reported elsewhere (Lamar, R. T., et al., supra, 1990). The PCP amended soils were prepared by adding PCP in acetone to obtain a final concentration of 100 µg g$^{-1}$. The moisture content of non-sterile Marshan and Batavia soils was adjusted to 48% of moisture (weight of moisture/weight of dry soil) with deionized water. The soils were inoculated with approximately 3% of fungal pellets or 3% of sterile pellets for control (dry weight of pellets/weight of dry soil). The inoculated soils were incubated in non-sterile jam jars at 24° C. in the dark (30 g soil per jar). Jars were equipped with modified covers to allow adequate air exchange, provided by a piece of microporous material over a 3.2 mm hole on the inside of the cover. Two replicates were prepared for each fungus-soil and control-soil culture.

L. PCP analyses. Two 5 g soil samples from each fungus and control soil culture were extracted and extracts analyzed by GC-ECD using the procedure described in Lamar, et al. (Lamar, R. T., et al., supra, 1993). In order to determine the efficiency of PCP extraction, the Marshan soil was spiked with 42500 dpm $^{14}$C [PCP]. 84.5±3.8% of radioactivity was recovered after the PCP extraction procedure. PCP was analyzed as the trimethylsilyl derivate and quantified using the trimethylsilyl derivate of 2,4,6,-tribromophenol as internal standard.

3. Results

A. Pelletized substrates. Substrate mixtures (Table 1) based on sawdust and/or rice hulls or a nutrient-fortified grain-sawdust mixture were successfully pelletized.

The mixtures based on sawdust or rice hulls require 3–4 passes through the pellet press to obtain pellets with desired properties. Only 1–2 passes were necessary for the production of pellets based on the nutrient-fortified grain sawdust mixture. Drying the pellets from an initial moisture content of approximately 30% to 3% to 10%, depending on the mixture, resulted in large increase in the mechanical strength of pellets (see Table 1, below).

TABLE 1

Mechanical strength of pelleted substrates before and after drying in a stream of hot air at 80° C. for 1 hour.

| Pelted substrate | % moisture Before drying | % moisture After drying | Strength of pellets before drying | Strength of pellets after drying |
|---|---|---|---|---|
| 75% sawdust 15% starch 8% corn meal 2% lignosulphonate | 27–30% | 6–10% | 7.0 ± 2.9 N 0.10 ± 0.02 J | 30.9 ± 11.9 N 0.32 ± 0.80 J |
| 75% rice hulls 15% starch 8% corn meal 2% lignosulphonate | 27.9% | 9.5% | 9.5 ± 2.0 N 0.059 ± 0.014 J | 26.9 ± 5.3 N 0.138 ± 0.031 J |
| 41.5% sawdust 41.5% rice hulls 10% starch 5% corn steep liquor 2% lignosulphonate | 28.2% | 7.4% | 7.3 ± 1.6 N 0.049 ± 0.014 J | 26.0 ± 4.9 N 0.151 ± 0.036 J |
| nutrient-fortified grain-sawdust mixture | 30% | 3% | 0.4 ± 0.12 N 0.0065 ± 0.002 J | 23.6 ± 2.6 N 0.04 ± 0.007 J |

B. Coating, inoculation, and over-growing of the pellets. Dried, sterile pellets were coated with a suspension of alginate hydrogel and conidia of *Phanerochaete chrysosporium*, chlamydospores and mycelium fragments of *Phanerochaete sordida*, and mycelium fragments of *Irpex lacteus*, *Bjerkandera adusta*, and *Trametes versicolor* (Table 2, below). Mycelial fragments of *T. versicolor* were found to need conditioning after fragmentation and prior to inoculation in alginate in order to maintain viability after spraying on pellets. The number of CFU in the alginate suspension of *Irpex lacteus* increased by spraying, most likely through further fragmentation of mycelial fragments. For other fungi no change in viability of biological material due to the spraying was found (Table 2).

TABLE 2

Coating, by spraying, the pelleted substrate with Na-alginate hydrogel, supplemented with various types of fungal biological material. The effect of spraying on viability of fungal biological material, expressed in Colony Forming Units.

| Fungus | Type of biological material | CFU of fungi in hydrogel before spraying | CFU of fungi in hydrogel after spraying | % viability of biological material after spraying |
|---|---|---|---|---|
| P. chrysosp. | conidia | $7.5 \pm 2.5*10^5$ CFU/mL | $7.5 \pm 1.8*10^5$ CFU/mL | 100% |
| P. sordida | mycelium and chlamyd. | $2.5*10^4$ CFU/mL | $2.5*10^4$ CFU/mL | 100% |
| I. lacteus | mycelium | $7.2 \pm 2*10^4$ CFU/mL | $1.8 \pm 0.3*10^5$ CFU/mL | 252% |
| B. adusta | mycelium | $9.0 \pm 3.0*10^4$ CFU/mL | $8.2 \pm 1.8*10^4$ CFU/mL | 91% |
| T. versicolor | mycelium | $13.5 \pm 0.6*10^5$ CFU/mL | $14.3 \pm 0.1*10^5$ CFU/mL | 106% |

Coated pellets were incubated until over-grown with fungal mycelia. The time needed for formation of an active fungal mycelial coat varied from 3 days for P. chrysosporium to 8 days for B. adusta (Table 3). The optimum temperature of incubation for the tested fungi was 30° C. except for B. adusta (24° C.). The lowest concentration of biological material in alginate hydrogel coating that still produced a mycelial coat on the surface of the pellets was also determined (Table 3). Pellets were typically coated with 20–30% of hydrogel (Table 6). At an average pellet weight of 0.2 g, 0.02 L (P. sordida) to 15.9 L (I. lacteus) of fungal growth medium was needed for production of biological material that would be required for inoculation of 1000 Kg of pellets (Table 3). During the over-growth period the fungal inoculum lost from 3% to 8% of moisture. The final moisture content of over-grown pellets was 32.8%, 28.0%, 20.7%, 22.5%, and 35.5% for pellets coated with Phanerochaete chrysosporium, Phanerochaete sordida, Irpex lacteus, Bjerkandera adusta, and Trametes versicolor, respectively.

Pellets thoroughly over-grown with fungal mycelium were considered ready for use as fungal inoculum for bioremediation of contaminated soils. Fungal inocula were further tested for contamination in soil, for mechanical strength, and for ability to deplete PCP from artificially contaminated soils.

C. Contamination in soil. Fungal inocula thoroughly over-grown with active fungal mycelium were highly resistant to contamination by indigenous soil bacteria and fungi when introduced into non-sterile soils (Table 4). Pellets coated with either Phanerochaete chrysosporium conidia or mycelial fragments of P. sordida and I. lacteus, but not overgrown with mycelium, were outcompeted by soil microflora and generally failed to survive and proliferate in the soil. The microbial contaminants identified to attack fungal inocula were mainly soilborne fungi (Table 4). The type of artificially contaminated soils and the geographical origin of soils from actual contaminated sites is presented in Table 5. The type and quantity of contamination, identified indigenous fungi, and field water capacity and the actual water content used are also shown (Table 5).

TABLE 3

Lowest concentration of fungal biological material in Na-alginate hydrogel coating, that still produce fungal mycelial coat over the pelleted substrate. Time of incubation and the superior tested T of incubation for development of mycelial coat. Amount of growth medium, surface area of 2% potato-dextrose agar for P. chrysosporium and volume of 2% malt extract, 2% glucose liquid media for other fungi, that provide sufficient amount of biological material for coating 1 ton of pellets.

| Fungus | Minimum conc. of biological material that produced a mycelial coat on pellets | T of incubation (°C.) | Time needed for development of mycelial coat on pellets surface | Growth medium for production of biological material for 1 ton of pellets |
|---|---|---|---|---|
| P. chrysosporium | 3200 conidia mL$^{-1}$ | 30 | 3 days | 198 cm$^2$ |
| P. sordida | $0.9*10^{-4}$ g L$^{-1}$ | 30 | 7 days | 0.02 L |
| I. lacteus | 0.085 g L$^{-1}$ | 30 | 5 days | 15.9 L |
| B. adusta | 0.0297 g L$^{-1}$ | 24 | 8 days | 6.5 L |
| T. versicolor | 0.1713 g L$^{-1}$ | 30 | 4 days | 7.23 L |

TABLE 4

The proliferation of indigenous fungi on fungal inocula introduced into artificially contaminated soils and into the soils from actual contaminated sites in Utah, Indiana, Mississippi, Wisconsin, and from two distinct sites in Florida. Pellets inoculated but not over-grown with active *P. chrysosporium* mycelium, and pellets over-grown with active mycelia of various fungi were used.

| Soil type (Origin) | % Contamination of pelleted fungal inoculum with indigenous fungi | | | | | |
|---|---|---|---|---|---|---|
| | P. chrysosporium not over-grown | P. chrysosporium over-grown | P. sordida over-grown | T. versicolor over-grown | I. lacteus over-grown | B. adusta over-grown |
| Marshan | 100[1] | 0 | 0 | 0 | 0 | 0 |
| Batavia | 0 | 0 | 0 | 0 | 0 | 0 |
| "Utah" | 100[1] | 0 | 0 | 0 | 0 | 0 |
| "Indiana" | 100[1] | 0 | 0 | 0 | 11[3] | 0 |
| "Florida A" | 100[1] | 0 | 11[1] | 0 | 0 | 0 |
| "Mississippi" | 92.7[2] | 0 | 0 | 0 | 0 | 0 |
| "Wisconsin" | 100[2] | 0 | 0 | 0 | 0 | 0 |
| "Florida B" | 100[2] | 0 | 0 | 0 | 0 | 0 |

Fungal inoculum contamination:
[1]Trichoderma spp., Fusarium spp.
[2]Fusarium spp.
[3]Trichoderma spp.

TABLE 5

The type and quantity of contamination of artificially contaminated soils and soils from actual contaminated sites, indigenous fungi isolated from these soils, field water holding capacity of the soils, and % of moisture of soils that was used, all dry soil based.

| Soil type (Origin) | Contaminants | Indigenous fungi | Field H$_2$O capacity | % of moisture used |
|---|---|---|---|---|
| Marshan | 100 µg/g PCP (added) | Fusarium spp. Penicillium spp. Aspergillus spp. Trichoderma spp. | 88.1% | 48% |
| Batavia | 100 µg/g PCP (added) | Penicillium spp. Mucor spp. | 67.5% | 48% |
| "Utah" | PCB[1] | Fusarium spp. Scytalidium spp. Trichoderma spp. Penicillium spp. | 23.9% | 19.4% |
| "Indiana" | <30 µg/g 2,4 dichloro-phenoxy-acetic acid | Mucor spp. Penicillinium spp. Trichoderma spp. Fusarium spp. | 55.7% | 26.3% |
| "Florida A" | 145 µg/g PCP, 65 µg/g PCA | Fusarium spp. Trichoderma spp. | 37.6% | 34.5% |
| "Mississippi" | 1200 µg/g PCP, PAR | Talaromyces spp. Fusarium spp. Aspergillus spp. Arthrinium spp. Bispora spp. Phialacephala spp. | 37% | 27.9% |
| "Wisconsin" | 200 µg/g PCP, 120 µg/g PCA | Fusarium spp. Penicllinium spp. | 17.2% | 14.2% |
| "Florida B" | 1200 µg/g PCP, PAH | Fusarium spp. Aspergillus spp. | 24.7% | 23.3% |

[1]polychlorinated biphenyls

D. Mechanical strength of the pelleted fungal inoculum. FIG. 3 presents the data obtained from the experiments that simulated inoculation of soil with fungal inoculum by mixing the pellets with soil and sand in a laboratory mixer.

FIG. 3 is a graph showing the decrease of initial dry weight of pellets with different mechanical strength after mixing 3% of pellets with 1 Kg of sand or soil during a 30 minute period. Referring to FIG. 3, Group A includes (□) pellets (17.5 N, 0.12 J) mixed with fine sand, (Δ) pellets (17.5 N, 0.11 J) mixed with sand with particles size over 2 mm, (x) pellets (17.5 N, 0.11 J) mixed with coarse sand, (◊) pellets (1.3 N, 0.04 J) mixed with Marshan soil with 40% moisture. Group B includes (◊) pellets (1.9 N, 0.02 J) mixed with Marshan soil with 40% moisture, (■) pellets (1.3N, 0.04 J) mixed with fine sand, (□) pellets (1.9 N, 0.02 J) mixed with fine sand, (A) pellets (1.3 N, 0.04 J) mixed with Marshan soil with 3.5% moisture, (x) pellets (1.3 N, 0.04 J) mixed with coarse sand, (◊) pellets (1.3 N, 0.04 J) mixed with sand with particles size over 2 mm, (Δ) pellets (1.3 N, 0.04 J) mixed with 3 Kg of coarse sand. Group C includes (■) pellets (1.9 N, 0.02 J) mixed with sand with particles size over 2 mm, (□) pellets (1.9 N, 0.02 J) mixed with coarse sand.

The pellets possessing a mechanical strength of 17.51±4.94 N or 0.11±0.02 J, which corresponded to the strength of dried pellets, did not suffer any material loss or structural damage during mixing with soil or sand. For successful mixing with soil, the mechanical strength of pelleted fungal inoculum must exceed 2 N and 0.04 J (FIG. 3). The mechanical strength of pelleted fungal inocula is presented in Table 6.

for the production of fungal spawn for supply to mushrooms growers, or rely on "bulking up" of pure cultures of selected fungi on large amounts of organic substrates and agricultural wastes. These techniques are labor intensive and quality of the inoculum produced is quite variable.

Pelleted fungal inocula, that consists of a pelleted core containing a carrier, nutrient source, binder and lubricant, that are encapsulated by a layer of mature fungal inoculum, can be produced from the same inexpensive materials as currently used inocula (see Table 1 and Amandus Kahl Nachf. *Pellets from municipal solid waste, waste paper, straw, peat, waste wood, filter dust, filter cake, FGD-gypsum, plastic waste, livestock feeds*, Hamburg, FRG). However, pelleted inocula can be produced with consistent quality because each inoculum possesses a specified ratio

TABLE 6

Percentages of Na-alginate hydrogel-fungal biomass suspension coating material on pellets and strength of pelleted fungal inocula after coating with hydrogel and after development of mycelial coat.

| Fungus | % of coating material on pellets | Strength of pellets after coating | Strength of pellets after over-growing |
|---|---|---|---|
| P. chrysosporium | 33 ± 1.9% | 8.7 ± 7 N<br>0.11 ± 0.02 J | 5.7 ± 1.2 N<br>0.06 ± 0.02 J |
| P. sordida | 27.7 ± 2.7% | 10.4 ± 2.0 N<br>0.10 ± 0.04 J | 8.3 ± 2.2 N<br>0.07 ± 0.02 J |
| I. lacteus | 19.8 ± 0.8% | 12.5 ± 2.2 N<br>0.11 ± 0.05 J | 10.5 ± 3.0 N<br>0.07 ± 0.02 J |
| B. adusta | 21.8 ± 1.7% | 14.5 ± 2.8 N<br>0.18 ± 0.05 J | 10.4 ± 2.0 N<br>0.16 ± 0.03 J |
| T. versicolor | 36.1 ± 0.5% | 9.7 ± 5 N<br>0.044 ± 0.013 J | 9.3 ± 2.3 N<br>0.05 ± 0.01 J |

Figure 5A:
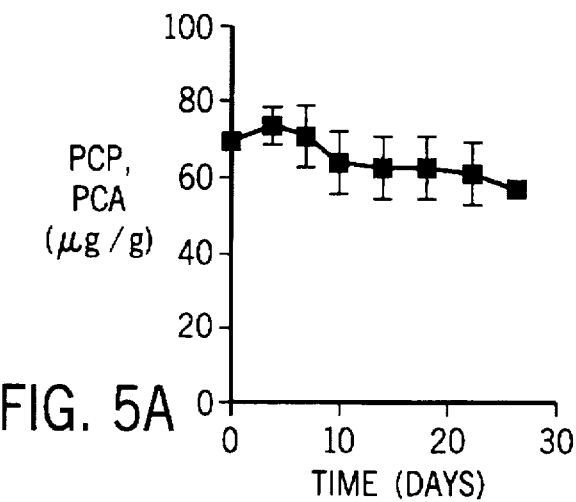
FIG. 5A–G demonstrates the depletion of PCP in soils supplemented with PCP and inoculated with pelleted fungal inoculum.

E. Removal of PCP from artificially contaminated soil. The decrease of PCP concentration was studied in the soils contaminated with 100 µg $g^{-1}$ PCP. Soils were inoculated with sterile non-coated pellets and with pellets over-grown with *Phanerochaete chrysosporium, Phanerochaete sordida, Irpex lacteus, Bjerkandera adusta*, and *Trametes versicolor*. In Marshan soils *P. chrysosporium* grew primarily in the area around the inserted pellets. Growth of *B. adusta* and *I. lacteus* was well-distributed through the soil surface, with some penetration into the depth of soil mass. The growth of *P. sordida* and *T. versicolor* was intermediate between the two extremes. In Batavia soil, *P. chrysosporium* colonize, only the surface close to the inserted pellets. The PCP concentration in Marshan soil inoculated with sterile pellets declined only slightly, as shown in FIG. 5A. Shortly after inoculation into the soil, Fusarium spp. were found growing on the pellets. In Batavia and Marshan soils inoculated with *P. chrysosporium*, the PCP concentration decreased by 61% and 85%, respectively, after 4 weeks.

Figure 5B:
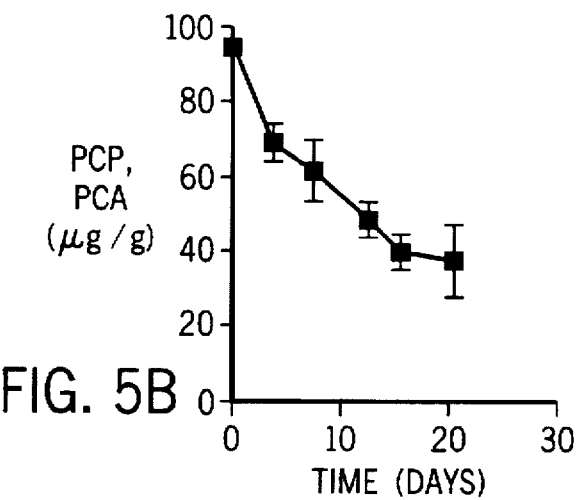
Figure 5C:
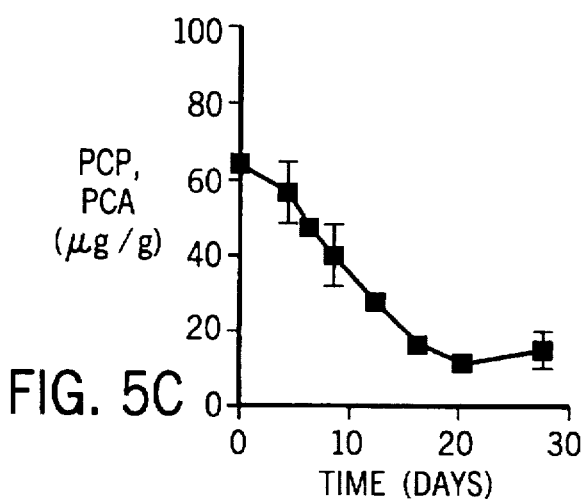
Figure 5D:
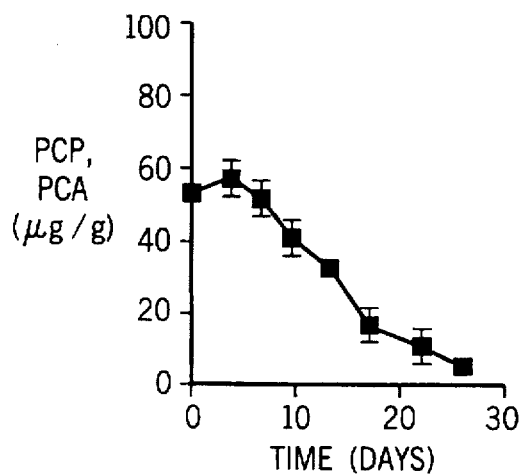
Figure 5E:
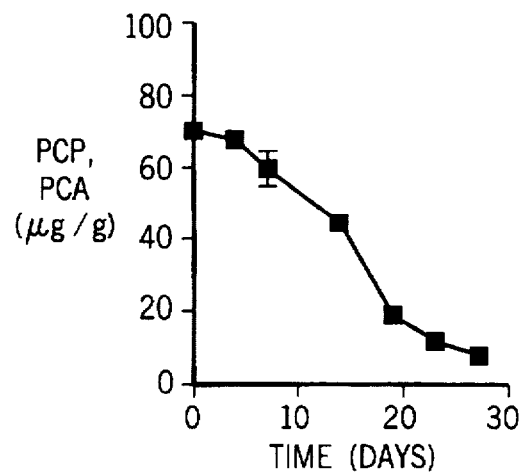
Figure 5F:
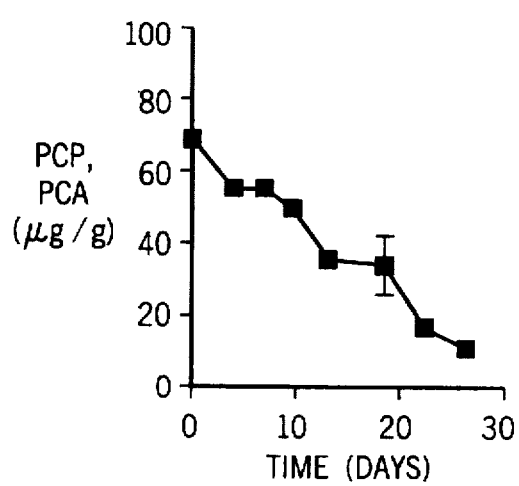
Figure 5G:
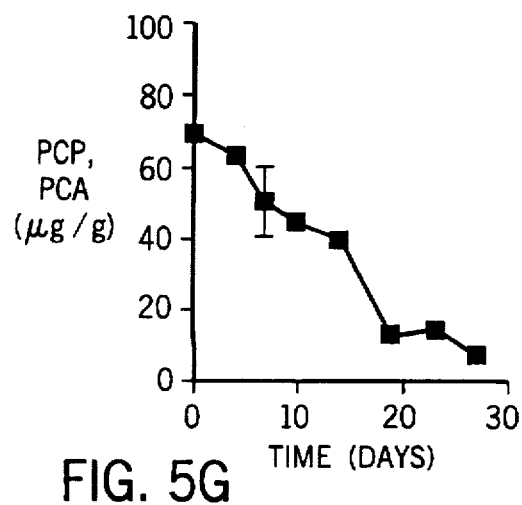

FIG. 5A–G demonstrates depletion of PCP in soils supplemented with 100 µg $g^{-1}$ PCP and inoculated with 3% of pelleted fungal inoculum. FIG. 5A indicates Marshan soil supplemented with sterile pellets; FIG. 5B indicates Batavia soil inoculated with *P. chrysosporium*; FIG. 5C indicates Marshan soil inoculated with *P. chrysosporium*. In Marshan soil inoculated with *P. sordida*, the PCP concentration decreased by 92%, as shown in FIG. 5D. In soils inoculated with pelleted fungal inoculum containing *I. lacteus, B. adusta*, and *T. versicolor*, the PCP concentration decreased by 86%, 82%, and 90%, respectively, after 4 weeks (FIGS. 5E, 5F, 5G).

4. Discussion

Currently used fungal inocula for bioaugmentation of contaminated soils are produced using techniques developed between the amounts of fungus and substrate for growth and activity. Therefore, the amount of growth and/or pollutant-degrading activity from each inoculum unit (i.e. pellet) can be predetermined and the quality of each inoculum batch evaluated.

The material composition of the pelleted fungal inocula can be tailored to a particular fungus to enhance biological potential of the inoculum. For example, growth of white-rot fungi and production of lignin-degrading enzymes, which are believed to be involved in xenobiotic degradation by these organisms (Lamar, R. T., et al., supra, 1992), are greatly affected by the ratio between and amounts and sources of carbon and nitrogen (Kirk, T. K., *In Microbial Degradation of Organic Compounds*, D. T. Gibson (ed.) Marcel Dekker, New York, p. 399–438, 1984). Therefore, fungal growth and pollutant-degrading abilities can be maximized by selecting substrates that provide the optimum mix of nutrients and sources.

Provision of adequate moisture to support fungal growth was achieved by coating and simultaneous inoculation of sterile pellets by spraying them with a suspension of Na-alginate hydrogel and fungal biomass. Coating pellets with Na-alginate-fungal biological material suspension allows different types of fungal biological material including conidia, chlamydospores and mycelial fragment, or only mycelial fragments, to be used (Table 2). Alginate hydrogels are not-toxic to microbes and are easy to prepare (Kester, J. J., et al., supra, 1986). They are cheaper than chitosan and agarose and do not need to be heated to 42° C. during preparation as does carrageenan (Trevors, J. T., et al., *Microb. Releases* 1:61–69, 1992).

The effectiveness of bioaugmentation depends on the survival and activity of inoculated microorganisms in soil.

Pellets over-grown with active fungi resisted attack from indigenous soil bacteria and fungi when introduced into a wide variety of non-sterile, contaminated soils (Table 5). The presence of the active mycelial coat on the pelleted substrate and unshared access of inoculated fungus to the nutrients in the pellet core seemed to provide a competitive advantage and thus may be important for survival and growth of the inoculated fungus (Bruehl, G. W., In G. W. Bruehl (ed.), *Biology and Control of Soil-Borne Plant Pathogens*. American Phytophatological Society, St. Paul, p. 77–83, 1975). In contrast, pellets that were coated with spores and slow growing mycelial fragments but were not over-grown, were unable to possess the substrates in pellets rapidly and became colonized themselves by indigenous microorganisms (Table 4). Fungal inocula in the form of spores or mycelium fragments are also much more sensitive to growth inhibition by contaminants, such as PCP, than actively growing fungal mycelium (Kennes, C., et al., *Biotechnol. Lett.* 16:759–764, 1994; Mileski, G. J., et al., *Appl. Environ. Microbiol.* 54:2885–2889, 1988; Morton, H. L., et al., *For. Prod. Jour.* 16:25–30, 1966). This is another possible reason for failure of not-over-grown fungal inoculum to survive and proliferate in soil.

One way to improve the economics of fungal bioaugmentation is to produce inocula with lower moisture content to decrease the cost of transportation. Current inoculum formulations (i.e. nutrient-fortified grain sawdust mixture) applied at a rate of 10 percent to a site that contained 100,000 cubic meters of contaminated soil required 25,000 tons wet weight of inoculum. The average moisture content of pelleted inocula varied from 20.7% of moisture for inoculum with *I. lacteus* to 35.5% for inoculum with *T. versicolor*, about half that of the nutrient-fortified grain-sawdust mixture (Lamar, R. T., et al., supra, 1994). A further decrease in cost of transportation and storage would be due to an increase in the specific weight of the pelleted substrates. Pelleted inoculum was approximately 50% reduced in volume compared to original substrate mixture.

Fungal inocula of sufficient mechanical strength are essential for maintaining inoculum potential in the process of collection, packing, transportation, and soil application. Mechanical strength of the inoculum is particularly important in the process of application of the inoculum into the soil where damage to fungal mycelia due to the grinding action of soil particles can reduce the inoculum potential. Inocula of proper mechanical strength could be used with conventional seed-sowing machinery or would simplify other delivery systems. Mechanical strength of the over-grown pelleted fungal inoculum varied from 5.7±1.2 N, 0.06±0.02 J for *P. chrysosporium* to 10.4±2.0 N, 0.16±0.03 J for *B. adusta* (Table 6). These strengths are substantially higher than strength (2 N, 0.04 J, FIG. 3) which was found inadequate for successful delivery of pellets into the soil.

The substrates could be, if necessary, shredded and crushed to obtain adequate size for pelleting, and then mixed in a large scale V shape mixers. One of the most expensive operations in fungal inocula production would be sterilization of substrate mixture. Methods such as autoclaving and steaming used by commercial mushroom growers for pasteurization of large amounts of solid substrates (Stamets, P., In P. Stamets (ed.), *Growing Gourmet and Medical Mushrooms*, Ten Speed Press, Berkeley, p. 161–178, 1933) could be employed. Alginate hydrogel can be sterilized by autoclaving or by γ irradiation (Trevors, J. T., et al., supra, 1992). For pelleting the sterile substrates, the industrial scale pellet press that is commonly found in chemical factories, plastic and food industries, agriculture, oil mills, woodpulp works, could be used. Sufficient mechanical strength of the pelleted substrates is necessary for the process of coating the pellets with hydrogel. Brittleness of pellets would prevent the coating process or increase hydrogel consumption. Properties of the substrate mixture such as moisture content, percentage of lubricant (e.g. lignosulfonate), and binder (e.g. starch), influence the quality and strength of pellets. The quality and strength of the pellets also depends on the type of bonding forces between the individual particles in the substrate mixture (i.e. capillary bonds, adhesion and cohesion, forces of attraction (van der Waals forces), solid body bridges, bonding due to felting of larger particles). These forces can be reinforced by optimizing the operating conditions of pellet press for various substrate mixtures (Amandus Kahl Nachf, supra). After pelleting the quality (mechanical properties, sterility) of pellets can also be improved by drying (Table 1). Dried pellets are also less susceptible to microbial contamination and can be stored with less risk of contamination than wet substrates. Fungal biomass for inoculating the pellets could be produced by submerged fermentation using inexpensive, readily available agricultural by-products with the appropriate nutrient balance. For example molasses, brewer's yeast, corn steep liquor, sulfite waste liquor, and cottonseed and soy flours could be used. The whole fermentation broth suspension could then be homogenized to fragment the fungal mycelia and incorporated into hydrogel coating. Biomass production may be an expensive step in fungal pellet production. However, as shown in Table 3, 0.02 L to 15.9 L of fungal growth medium would be sufficient for production of biomass for inoculation of 1000 Kg of pellets. For uniform coating of the pellets with hydrogel, a fluidized bed coating machine, as used in pharmaceutical industries for coating of tablets etc., but adjusted to work with hydrogel (Abletshuauser, C. B., et al., supra, 1993) could be utilized.

Formed pelleted inoculum with several different white-rot fungi was tested for its ability to deplete PCP from soils (FIG. 5). In Marshan soils with *Irpex lacteus*, *Bjerkendera adusta*, and *Trametes versicolor* 82–90% of PCP was depleted (FIGS. 5E, 5F, 5G) in four weeks.

We claim:

1. A fungal inoculum comprising a pelleted substrate having a mechanical strength of at least 0.04 Joules coated with fungal propagules suspended in a hydrophilic material.

2. The inoculum of claim 1 wherein the hydrophilic material comprises a hydrogel.

3. The inoculum of claim 2 wherein the hydrogel is selected from the group consisting of alginate and alginic acid.

4. The inoculum of claim 1 wherein the pelleted substrate comprises a lubricant.

5. The inoculum of claim 4 wherein the lubricant is lignosulphonate.

6. The inoculum of claim 1 wherein the substrate comprises a structural matrix and a nutrient and wherein the structural matrix comprises a material selected from the group consisting of sawdust, rice hulls, ground corn cobs, corn fiber, nut hulls and soybean hulls.

7. The inoculum of claim 6 wherein the nutrient is selected from the group consisting of starch, corn meal, and corn steep liquor.

8. The inoculum of claim 1 wherein the propagules comprise mycelium.

9. The inoculum of claim 1 wherein the pelleted substrate has been incubated until overgrown with fungal mycelium.

10. The inoculum of claim 9 wherein the propagules are selected from the group consisting of mycelia, conidia, and chlamydospores.

* * * * *